US009422329B2

(12) United States Patent
Falkenstein et al.

(10) Patent No.: US 9,422,329 B2
(45) Date of Patent: Aug. 23, 2016

(54) OPTIMIZED METHOD FOR ANTIBODY CAPTURING BY MIXED MODE CHROMATOGRAPHY

(75) Inventors: Roberto Falkenstein, Munich (DE); Thorsten Lemm, Kochel am See (DE); Markus Strasser, Penzberg (DE); Hidenari Yamada, Tokyo (JP)

(73) Assignee: Hoffmann-La Roche Inc., Nutley, NJ (US)

( * ) Notice: Subject to any disclaimer, the term of this patent is extended or adjusted under 35 U.S.C. 154(b) by 346 days.

(21) Appl. No.: 13/883,243

(22) PCT Filed: Nov. 2, 2011

(86) PCT No.: PCT/EP2011/069202
§ 371 (c)(1),
(2), (4) Date: May 2, 2013

(87) PCT Pub. No.: WO2012/059495
PCT Pub. Date: May 10, 2012

(65) Prior Publication Data
US 2013/0217866 A1    Aug. 22, 2013

(30) Foreign Application Priority Data
Nov. 5, 2010    (EP) ..................................... 10190192

(51) Int. Cl.
*C07K 1/18* (2006.01)
*C07K 1/16* (2006.01)
*C07K 16/06* (2006.01)

(52) U.S. Cl.
CPC .............. *C07K 1/18* (2013.01); *C07K 16/065* (2013.01)

(58) Field of Classification Search
None
See application file for complete search history.

(56) References Cited

U.S. PATENT DOCUMENTS

2003/0229212 A1*   12/2003   Fahrner et al. ............... 530/417
2010/0113746 A1*   5/2010    Lali et al. .................. 530/387.1

FOREIGN PATENT DOCUMENTS

| WO | 2008/073620 A2 | 6/2008 |
| WO | 2008/086335    | 7/2008 |
| WO | 2008/141824 A2 | 11/2008 |
| WO | 2009007451     | 1/2009 |
| WO | 2009/024620    | 2/2009 |
| WO | 2009/074634    | 6/2009 |
| WO | 2009/111347    | 9/2009 |
| WO | 2009/156430    | 12/2009 |
| WO | 2010/080062 A1 | 7/2010 |

OTHER PUBLICATIONS

Beck et al. "Characterization by liquid chromatography combined with mass spectrometry of monoclonal anti-IGF-1 receptor antibodies produced in CHO and NS0 cells" J. Chromatography B, 819 (2005) 203-218.*
The English translation of the Japanese Office Action, issued on Sep. 30, 2014, in the corresponding Japanese Patent Application No. 2013-537121.
The International Search Report and Written Opinion, issued on Dec. 30, 2011, in the corresponding PCT Patent Application No. PCT/EP2011/069202.
The English translation of the Japanese Office Action, issued on Sep. 8, 2015, in the corresponding Japanese Patent Application No. 2013-537121.
Gagnon et al., "Minibodies and Multimodal Chromatography Methods: A Convergence of Challenge and Opportunity," Bioprocess Int. Feb. 2010; 8(2): 26-35.
Chhatre et al., "A microscale approach for predicting the performance of chromatography columns used to recover therapeutic polyclonal antibodies," J. Chromatography A 1216 (2009) 7806-7815.

* cited by examiner

*Primary Examiner* — Daniel E Kolker
*Assistant Examiner* — James Rogers (57) ABSTRACT

Herein is reported a method for the purification of an antibody directly captured from clarified cell culture supernatants using Streamline CST and/or Capto MMC, wherein especially product related (aggregates and fragments) and process related impurities (host cell protein, media components) could efficiently be removed, resulting in a preparation with a purity comparable to classical protein A affinity chromatography.

11 Claims, 5 Drawing Sheets

OPTIMIZED METHOD FOR ANTIBODY CAPTURING BY MIXED MODE CHROMATOGRAPHY

CROSS-REFERENCE TO RELATED APPLICATIONS

This Application is a 35 U.S.C. §371 national stage application of International Patent Application PCT/EP2011/069202 (published WO2012/059495), filed Nov. 2, 2011, which claims priority of European Application 10190192.4, filed Nov. 5, 2010. The entire disclosure of each prior mentioned application is hereby incorporated by reference.

Herein is reported a method for the purification of an antibody directly captured from clarified cell culture supernatants using Streamline CST and/or Capto MMC, wherein especially product related (aggregates and fragments) and process related impurities (host cell protein, DNA, media components) could efficiently be removed, resulting in a preparation with a purity comparable to classical protein A affinity chromatography.

BACKGROUND OF THE INVENTION

Protein A chromatography is routinely employed as a first capture step in industrial monoclonal antibody purification processes due to its high selectivity, resulting in good overall yields and purities. However, a major drawback of this affinity chromatography is its high price, which especially in case of therapeutic antibodies needed at high doses and/or for chronic administration can account for a significant cost of goods factor. In addition, leached protein A ligand from the affinity matrix must be removed by further chromatography steps due to its potential immunogenicity.

Mixed mode chromatography on multimodal resins exhibiting ionic and hydrophobic functionalities can offer a valuable alternative to the classical affinity approach. Due to the salt tolerability of the hydrophobic component, in most cases a direct loading of the clarified cell culture supernatant on the matrix is possible resulting in an effective capturing the monoclonal antibody. However, due to the multimodal nature of the resin, different types of interaction of the ligand with a particular monoclonal antibody are possible, requiring unique wash and elution condition differing from traditional ion-exchange or hydrophobic interaction chromatography.

In WO 2010/080062 a separation method using single polymer phase systems is reported. A manufacturing process for the production of polypeptides expressed in insect cell lines is reported in WO 2008/073620.

SUMMARY OF THE INVENTION

It has been found that a multimodal weak cation exchange chromatography material can be used as first step in a column chromatography purification method directly with crude cell culture cultivation supernatant.

One aspect reported herein is a method for producing an anti-IGF-1R antibody comprising the following steps:
a) applying a crude mammalian cell culture cultivation supernatant to a multimodal weak cation exchange chromatography material,
b) recovering the anti-IGF-1R antibody by applying a buffered solution comprising ethylene glycol and an inorganic salt to the multimodal weak cation exchange chromatography material and thereby producing an anti-IGF-1R antibody.

In one embodiment the method comprises the following additional step a-1) prior to step a):
a-1) applying a buffered solution comprising an inorganic salt to the multimodal weak cation exchange chromatography material.

In one embodiment the method comprises the following additional step a-b) after step a) and prior to step b):
a-b) applying a buffered solution to the multimodal weak cation exchange chromatography material, whereby the anti-IGF-1R antibody is not recovered from the multimodal weak cation exchange chromatography material.

In one embodiment the step a-b) comprises two steps a-b1) and a-b2):
a-b1) applying a buffered solution comprising an inorganic salt to the multimodal weak cation exchange chromatography material, and
a-b2) applying a buffered solution comprising a denaturant to the multimodal weak cation exchange chromatography material,
whereby the anti-IGF-1R antibody is not recovered from the multimodal weak cation exchange chromatography material.

In one embodiment the denaturant is selected from guanidinium hydrochloride, and urea.

In one embodiment the inorganic salt is selected from sodium chloride, potassium chloride, and ammonium chloride.

In one embodiment the buffered solution in step b) comprises 20 mM to 30 mM Tris, 1050 mM to 1350 mM sodium chloride, and about 20% (w/v) ethylene glycol at a pH value of from pH 7.1 to pH 7.3.

In one embodiment the buffered solution in step a-1) comprises 20 mM to 30 mM Tris, and 80 mM to 120 mM sodium chloride at a pH value of from pH 7.1 to pH 7.3. In one embodiment the buffered solution in step a-b1) comprises 20 mM to 30 mM Tris, and 80 mM to 120 mM sodium chloride at a pH value of from pH 7.1 to pH 7.3. In one embodiment the buffered solution in step a-b2) comprises 110 mM to 140 mM Tris, 80 mM to 120 mM sodium chloride, and 30 mM to 40 mM of arginine at a pH value of from pH 7.1 to pH 7.3.

In one embodiment the multimodal weak cation exchange chromatography material comprises cross-linked agarose to which a carboxylic acid, ether, thioether and aromatic functional group containing multimodal weak cation exchange ligand is covalently attached.

DETAILED DESCRIPTION OF THE INVENTION

Herein is reported a process for the purification of a monoclonal antibody captured from clarified cell culture supernatants using Streamline CST and/or Capto MMC comprising optimized conditions for elution and washing. Especially product related (aggregates and fragments) and process related impurities (host cell protein, media components) can efficiently be removed, resulting in a preparation with a purity comparable to classical affinity chromatography. Thus, with the method as reported herein a classical protein A affinity chromatography can be replaced.

In one embodiment the method does not comprise a protein A affinity chromatography step.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds.), John Wiley & Sons, Inc., New York (1987).

The term "applying to" denotes a partial step of a purification method in which a solution is brought in contact with a chromatography material. This denotes that either a) the solution is added to a chromatographic device in which the chromatography material is contained, or b) that the chromatography material is added to the solution. In case a) the solution passes through the device allowing for an interaction between the chromatography material and the substances contained in solution. Depending on the conditions, such as e.g. pH, conductivity, salt concentration, temperature, and/or flow rate, some substances of the solution can be bound to the chromatography material and other substances can be recovered from the chromatography material. The substances remaining in solution or recovered from the chromatography material can be found in the flow-through. The "flow-through" denotes the solution obtained after the passage of the device, which may either be the applied solution or a buffered solution, which is used to wash the column or to cause elution of substances bound to the chromatography material. In one embodiment the device is a column or a cassette. In case b) the chromatography material can be added, e.g. as a solid, to the solution, e.g. containing the substance of interest to be purified, allowing for an interaction between the chromatography material and the substances in solution. After the interaction the chromatography material is removed, e.g. by filtration, and the substance bound to the chromatography material are also removed therewith from the solution whereas the substances not bound to the chromatography material remain in solution.

The term "bind-and-elute mode" denotes an operation mode of a chromatography step, in which a solution containing a substance of interest to be purified is applied to a chromatography material, whereby the substance of interest binds to the chromatography material. Thus, the substance of interest is retained on the chromatography material whereas substances not of interest are removed with the flow-through or the supernatant. The substance of interest is afterwards recovered from the chromatography material in a second step with an elution solution. In one embodiment the method as reported herein is operated in bind-and-elute mode.

The term "buffered solution" denotes a solution in which changes of pH due to the addition or release of acidic or alkaline substances is leveled by the dissolved buffer substance. Any buffer substance with such properties can be used. Generally pharmaceutically acceptable buffers substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (Tris) buffered solution. In another embodiment the buffer solution is selected from a Tris buffered solution, or a citrate buffered solution, or a histidine buffered solution. The buffered solution may comprise an inorganic salt, such as e.g. sodium chloride, sodium sulphate, potassium chloride, potassium sulfate, ammonium chloride, or ammonium sulfate.

The terms "continuous elution" and "continuous elution method", which are used interchangeably within this application, denote a method wherein the conductivity of a solution causing elution, i.e. the recovery of a bound compound from a chromatography material, is changed, i.e. raised or lowered, continuously, i.e. the concentration is changed by a sequence of small steps each not bigger than a change of 2%, or of 1% of the concentration of the substance causing elution. In this "continuous elution" one or more conditions, for example the pH, the ionic strength, concentration of a salt, and/or the flow of a chromatography, may be changed linearly or exponentially or asymptotically. In one embodiment the change is linear.

The term "step elution" denotes a method wherein e.g. the concentration of a substance causing elution, i.e. the recovery of a bound substance from a chromatography material, is raised or lowered at once, i.e. directly from one value/level to the next value/level. In this "step elution" one or more conditions, for example the pH, the ionic strength, concentration of a salt, and/or the flow of a chromatography, can be changed all at once from a first, e.g. starting, value to a second, e.g. final, value. Thus, the conditions are changed incrementally, i.e. stepwise, in contrast to a linear change.

The term "multimodal weak cation exchange chromatography material" denotes an immobile high molecular weight matrix, such as chemically cross-linked agarose, that carries covalently bound charged substituents used as stationary phase in ion exchange chromatography. For overall charge neutrality not covalently bound counter ions are bound thereto. The "multimodal weak cation exchange chromatography material" has the ability to exchange its not covalently bound cationic counter ions for similarly charged ions of the surrounding solution. A "multimodal weak cation exchange chromatography material" comprises covalently bound ligands that are capable of exerting ionic interactions, hydrophobic interactions, van-der-Waals interactions as well as the formation of hydrogen bonds with molecules comprised in a surrounding solution.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "under conditions suitable for binding" and grammatical equivalents thereof as used within this application denotes that a substance of interest, e.g. an anti-IGF-1R antibody, binds to a stationary phase when brought in contact with it, e.g. an ion exchange material. This does not necessarily denote that 100% of the substance of interest is bound but essentially 100% of the substance of interest is bound, i.e. at least 50% of the substance of interest is bound, preferably at least 75% of the substance of interest is bound, preferably at least 85% of the substance of interest is bound, more preferably more than 95% of the substance of interest is bound to the stationary phase.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Naturally occurring antibodies are molecules with varying structures. For example, native IgG antibodies are hetero tetrameric glycoproteins of about 150,000 Daltons, composed of two identical light chains and two identical heavy chains that are disulfide-bonded. From N- to C-terminus, each heavy chain has a variable domain (VH), also called a variable heavy domain or a heavy chain variable domain, followed by three or four constant domains (CHL CH2, CH3 and optionally CH4). Similarly, from N- to C-terminus, each light chain has a variable domain (VL), also called a variable light domain or a light chain variable domain, followed by a constant light chain (CL) domain. The light chain of an antibody may be assigned to one of two types, called kappa (κ) and lambda (λ), based on the amino acid sequence of its constant domain.

Human insulin-like growth factor I receptor (IGF-IR, EC 2.7.112, CD 221 antigen) belongs to the family of transmembrane protein tyrosine kinases (LeRoith, D., et al., Endocrin. Rev. 16 (1995) 143-163; Adams, T. E., et al., Cell. Mol. Life Sci. 57 (2000) 1050-1063). IGF-IR binds IGF-I with high affinity and initiates the physiological response to this ligand in vivo. IGF-IR also binds to IGF-II, however with slightly lower affinity. IGF-IR overexpression promotes the neoplastic transformation of cells and there exists evidence that IGF-IR is involved in malignant transformation of cells and is therefore a useful target for the development of therapeutic agents for the treatment of cancer (Adams, T. E., et al., Cell. Mol. Life Sci. 57 (2000) 1050-1063). Exemplary anti IGF-1R antibodies, their encoding sequences and methods of production are reported in WO 2004/087756, WO 2007/045456, and WO 2007/115814.

For the purification of immunoglobulins or immunoglobulin fragments, which have been produced e.g. by cell cultivation methods, generally a combination of different chromatography steps is employed. Normally a protein A affinity chromatography is followed by one or two additional separation steps. In one embodiment said additional chromatography steps are a cation and an anion exchange chromatography step or vice versa. The final purification step is a so called "polishing step" for the removal of trace impurities and contaminants like aggregated immunoglobulins, residual HCP (host cell protein), DNA (host cell nucleic acid), viruses, or endotoxins. In one embodiment the final purification step is an anion exchange chromatography in flow-through mode.

It has been found that a multimodal weak cation exchange chromatography material can be used as first step in a column chromatography purification method directly with crude cell culture cultivation supernatant instead of the commonly used protein A affinity chromatography.

One aspect reported herein is a method for producing an anti-IGF-1R antibody comprising the following steps:
a) applying a crude mammalian cell culture cultivation supernatant to a multimodal weak cation exchange chromatography material,
b) recovering the anti-IGF-1R antibody by applying a buffered solution comprising ethylene glycol and an inorganic salt to the multimodal weak cation exchange chromatography material and thereby producing an anti-IGF-1R antibody.

For the method as reported herein no pre-conditioning of the crude cultivation supernatant is required. This was surprising as for cultivation supernatants obtained from cultivations, in which a different antibody has been produced, at least a reduction of the conductivity is required in order to allow a capturing of the antibody directly from the culture supernatant. Additionally the capturing of the anti-IGF-1R antibody from the crude cell cultivation supernatant is almost quantitatively. As the generally applicable conditions for the recovery of polypeptides from cation exchange chromatography materials and the conditions for binding by hydrophobic interactions to the multimodal weak cation exchange chromatography material point in opposite directed novel conditions for the recovery of an antibody from the multimodal weak cation exchange chromatography material were needed.

In one embodiment the method comprises the following additional step a-1) prior to step a):
a-1) applying a buffered solution comprising an inorganic salt to the multimodal weak cation exchange chromatography material.

In another embodiment the method comprises the following additional step a-b) after step a) and prior to step b):
a-b) applying a buffered solution to the multimodal weak cation exchange chromatography material, whereby the anti-IGF-1R antibody is not recovered from the multimodal weak cation exchange chromatography material.

In a further embodiment the step a-b) comprises two steps a-b1) and a-b2):
a-b1) applying a buffered solution comprising an inorganic salt to the multimodal weak cation exchange chromatography material, and
a-b2) applying a buffered solution comprising a denaturant to the multimodal weak cation exchange chromatography material,
whereby the anti-IGF-1R antibody is not recovered from the multimodal weak cation exchange chromatography material.

In also an embodiment the denaturant is selected from guanidinium hydrochloride, urea, and arginine. In one embodiment the inorganic salt is selected from sodium chloride, potassium chloride, and ammonium chloride. In also an embodiment the buffered solution in step b) comprises 20 mM to 30 mM Tris, 1050 mM to 1350 mM sodium chloride, and about 20% (w/v) ethylene glycol at a pH value of from pH 7.1 to pH 7.3. In one embodiment the buffered solution in step a-1) comprises 20 mM to 30 mM Tris, and 80 mM to 120 mM sodium chloride at a pH value of from pH 7.1 to pH 7.3. In a further embodiment the buffered solution in step a-b1) comprises 20 mM to 30 mM Tris, and 80 mM to 120 mM sodium chloride at a pH value of from pH 7.1 to pH 7.3. In another embodiment the buffered solution in step a-b2) comprises 110 mM to 140 mM Tris, 80 mM to 120 mM sodium chloride, and 30 mM to 40 mM arginine at a pH value of from pH 7.1 to pH 7.3. In still another embodiment the multimodal weak cation exchange chromatography material comprises cross-linked agarose to which a carboxylic acid, ether, thioether and aromatic functional group containing multimodal weak cation exchange ligand is covalently attached. In one embodiment a total volume of five column volumes of the buffered solution in step a-1) is applied to the multimodal weak cation exchange chromatography material. In another embodiment a total volume of five column volumes of the buffered solution in step a-b1) is applied to the multimodal weak cation exchange chromatography material. In also an embodiment a total volume of ten column volumes of the buffered solution in step a-b2) is applied to the multimodal weak cation exchange chromatography material. In still an embodiment a total volume of ten column volumes of the buffered solution in step b) is applied to the multimodal weak cation exchange chromatography material.

It has been found that the individual components of the buffered solutions have the following effects:

|  |  | Yield | LMWs | HMWs | Purity |
|---|---|---|---|---|---|
| Salt | NaCl | − | − | 0 | + |
|  | NH4Cl | −− | − | + | + |
|  | ethylene glycol | − | 0 | 0 | 0 |
| Denaturant | Urea | −− | − | 0 | + |
|  | Arginine | − | − | 0 | + |

+: increase; −: decrease; 0: no effect

The following examples and figures are provided to aid the understanding of the present invention, the true scope of which is set forth in the appended claims. It is understood that modifications can be made in the procedures set forth without departing from the spirit of the invention.

EXAMPLE

Materials & Methods

If not otherwise indicated have the different methods been performed according to the material manufacturer's manual.

Recombinant DNA Techniques:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Protein Determination:

Protein concentration was determined by determining the optical density (OD) at 280 nm, with a reference wavelength of 320 nm, using the molar extinction coefficient calculated on the basis of the amino acid sequence.

Size-Exclusion-HPLC:

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany).

Reversed Phase HPLC (RP-HPLC):

The purity is analyzed by RP-HPLC. The assay is performed on a Poroshell column using an acetonitrile/aqueous TFA gradient. The elution profile is monitored as UV absorbance at 215 nm. The percentages of the eluted substances are calculated based upon the total peak area of the eluted proteins.

DNA-Threshold-System:

see e.g. Merrick, H., and Hawlitschek, G., Biotech Forum Europe 9 (1992) 398-403

Host Cell Protein Determination:

The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

Example 1

Figure 1:
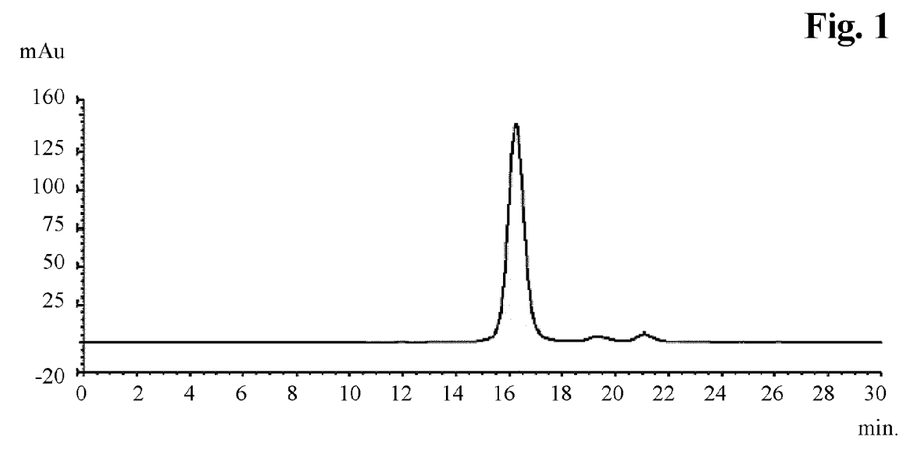
FIG. 1 Analytical size exclusion chromatogram of the anti-IGF-1R antibody chromatography eluate obtained in step b) of Example 1.

Chromatography of an Anti-IGF-1R Antibody with a Method as Reported Herein on the Multimodal Weak Cation Exchange Chromatography Material Capto™ MMC The chromatography was performed with the following parameters:
resin: Capto™ MMC
column diameter: 1 cm
bed height: 14.6 cm
applied solution: crude cell cultivation supernatant
load: 30 mg antibody per ml of material
step a-1) 25 mM Tris-HCl, 100 mM NaCl, pH 7.1
step a-b1) 25 mM Tris-HCl, 100 mM NaCl, pH 7.1
step b) 25 mM Tris-HCl, 1200 mM NaCl, 20% (w/v) ethylene glycol, pH 7.2
elution method: step elution
flow rate: 250 cm/h The analytical size exclusion chromatogram of the obtained antibody is shown in FIG. 1.

| buffered solution of step b) | | | | analytical SEC results of recovered antibody | | | |
|---|---|---|---|---|---|---|---|
| Tris [mM] | NaCl [mM] | ethylene glycol [wt %] | pH | total HMW [%] | antibody [%] | total HMW [%] | recovery [%] |
| 25 | 1200 | 20 | 7.2 | 1.6 | 91.8 | 6.7 | |

Example 2

Comparative Chromatographies to Example 1 of an Anti-IGF-1R Antibody with Conditions Different from the Method as Reported Herein on the Multimodal Weak Cation Exchange Chromatography Material Capto™ MMC The chromatography was performed with the following parameters:

resin: Capto™ MMC
column diameter: 1 cm
bed height: 14.6 cm
applied solution: crude cell cultivation supernatant
load: 30 mg antibody per ml of material
step a-1) 25 mM Tris-HCl, 100 mM NaCl, pH 7.1
step a-b1) 25 mM Tris-HCl, 100 mM NaCl, pH 7.1
step b) variable—see table below
elution method: step elution
flow rate: 250 cm/h From the table presented below it can be seen that with slightly different conditions of step b) the purification could be performed less effective.

| buffered solution of step b) | | | | analytical SEC results of recovered antibody | | | |
|---|---|---|---|---|---|---|---|
| Tris [mM] | NaCl [mM] | ethylene glycol [wt %] | pH | total HMW [%] | antibody [%] | total HMW [%] | recovery [%] |
| 300 | 1500 | 20 | 8.9 | 5.1 | 85.4 | 9.5 | 93 |
| 300 | 1500 | 20 | 7.1 | 4.7 | 85.6 | 9.7 | 95 |
| 300 | 1500 | 0 | 7.1 | 3.4 | 87.0 | 3.8 | 90 |
| 25 | 1500 | 20 | 8.9 | 4.6 | 86.3 | 9.2 | 101 |
| 25 | 1500 | 20 | 7.1 | 3.7 | 86.8 | 9.5 | 95 |
| 25 | 250 | 20 | 7.1 | 2.4 | 56.4 | 41.3 | 8 |
| 25 | 250 | 0 | 7.1 | 3.5 | 41.0 | 45.6 | 3 |

Example 3

Figure 2:
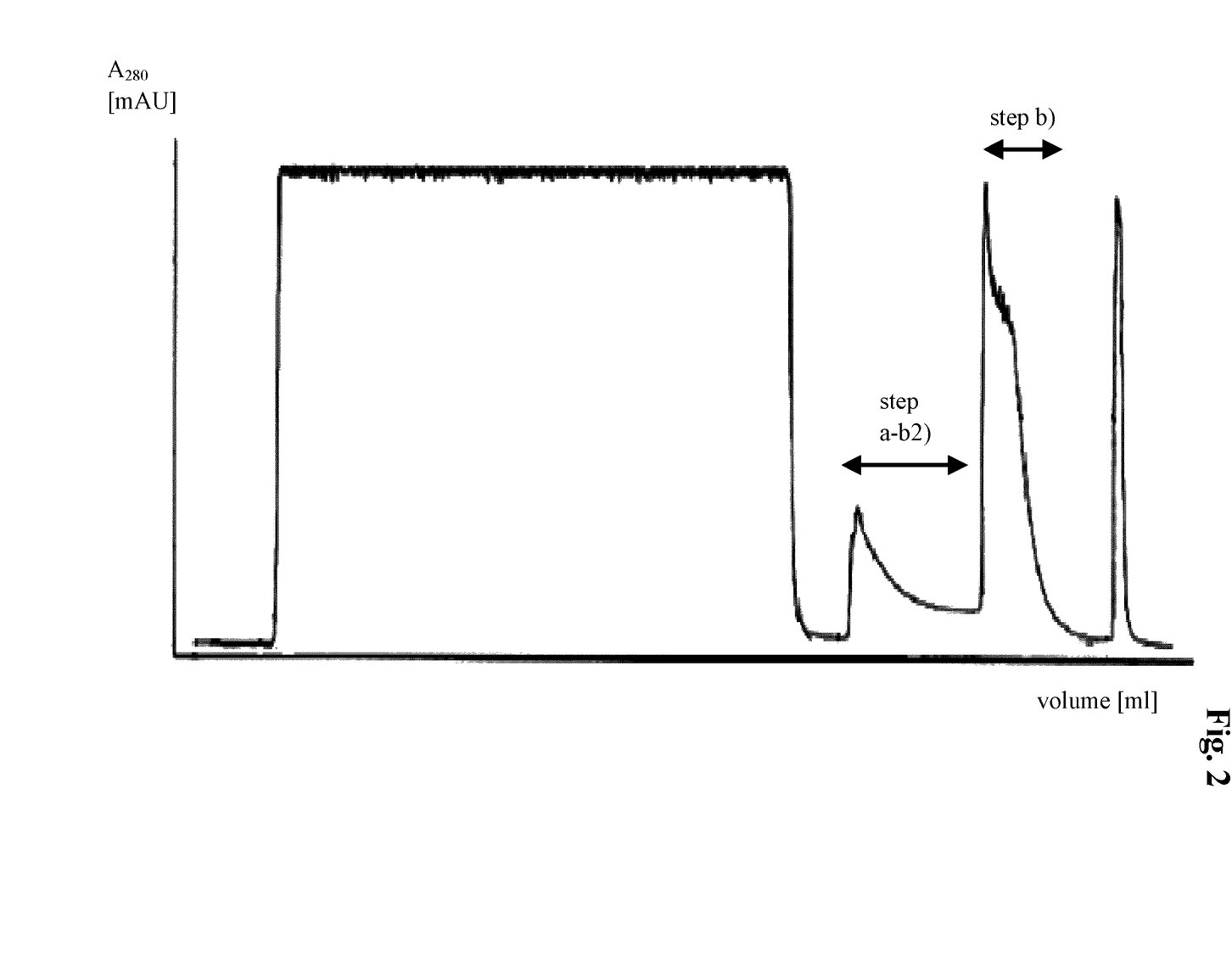
FIG. 2 Elution chromatogram of the anti-IGF-1R antibody obtained with a method as reported herein according to the conditions denoted in Example 3.
Figure 3:
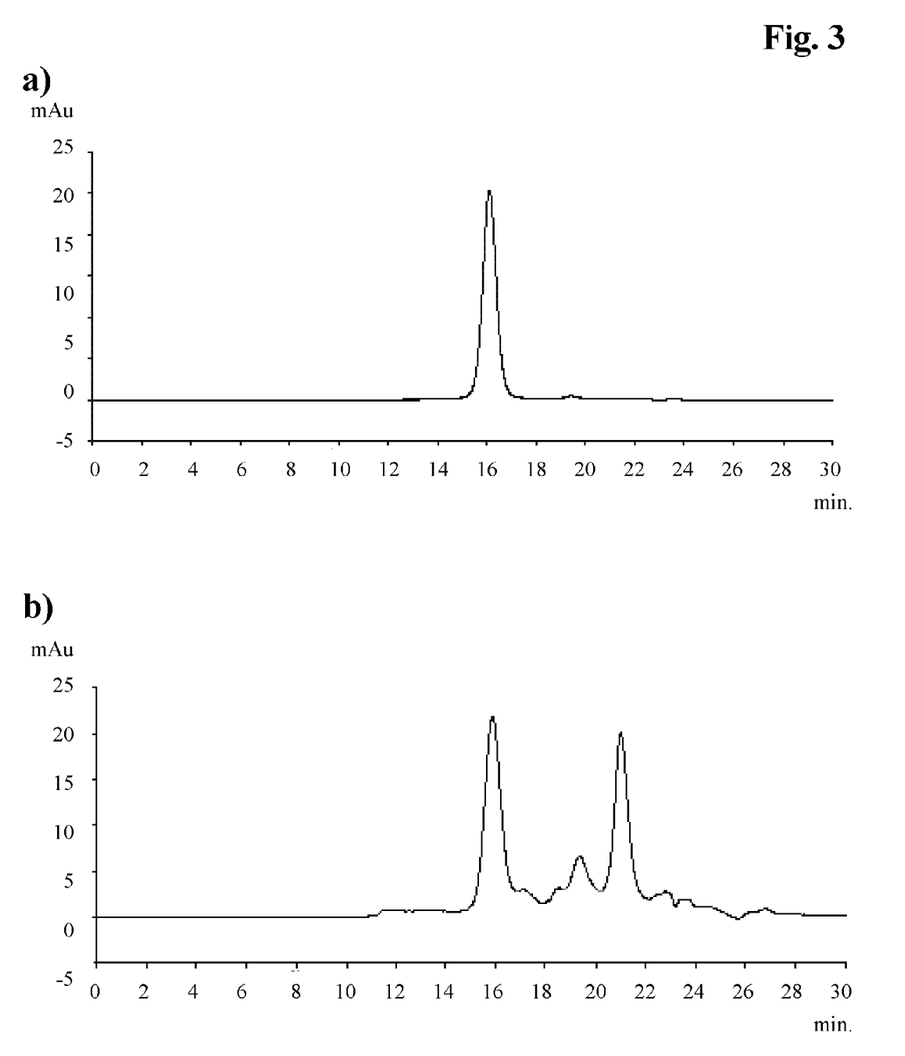
FIG. 3 Analytical size exclusion chromatogram of the anti-IGF-1R antibody chromatography eluate obtained in step b) (a) and for the eluate obtained in step a-b2) (b).

Chromatography of an Anti-IGF-1R Antibody with a Method as Reported Herein on the Multimodal Weak Cation Exchange Chromatography Material Capto™ MMC The chromatography was performed with the following parameters:
resin: Capto™ MMC
column diameter: 1 cm
bed height: 14.6 cm
applied solution: crude cell cultivation supernatant
load: 30 mg antibody per ml of material
step a-1) 25 mM Tris-HCl, 100 mM NaCl, pH 7.1
step a-b1) 25 mM Tris-HCl, 100 mM NaCl, pH 7.1
step a-b2) 125 mM Tris-HCl, 100 mM NaCl, 38 mM arginine, pH 8.7
step b) 25 mM Tris-HCl, 1200 mM NaCl, 20% (w/v) ethylene glycol, pH 7.2
elution method: step elution
flow rate: 250 cm/h The corresponding elution diagram is shown in FIG. 2 and the analytical size exclusion chromatogram for step b) in FIG. 3a and for step a-b2) in FIG. 3b).

| buffered solution of step a-b2) | | | | analytical SEC results of recovered antibody | | | |
|---|---|---|---|---|---|---|---|
| Tris [mM] | NaCl [mM] | arginine [wt %] | pH | total LMW [%] | antibody [%] | total HMW [%] | recovery [%] |
| 125 | 100 | 38 | 8.7 | 1.6 | 95.7 | 2.7 | 93 |

Example 4

Comparative Chromatographies to Example 3 of an Anti-IGF-1R Antibody with Conditions Different from the Method as Reported Herein on the Multimodal Weak Cation Exchange Chromatography Material Capto™ MMC The chromatography was performed with the following parameters:
resin: Capto™ MMC
column diameter: 1 cm
bed height: 14.6 cm
applied solution: crude cell cultivation supernatant
load: 30 mg antibody per ml of material
step a-1) 25 mM Tris-HCl, 100 mM NaCl, pH 7.1
step a-b1) 25 mM Tris-HCl, 100 mM NaCl, pH 7.1
step a-b2) variable—see table below
step b) 25 mM Tris-HCl, 1200 mM NaCl, 20% (w/v) ethylene glycol, pH 7.2
elution method: step elution
flow rate: 250 cm/h From the table presented below it can be seen that with slightly different conditions of step b) the purification could be performed less effective.

| buffered solution of step a-b2) | | | | analytical SEC results of recovered antibody | | | |
|---|---|---|---|---|---|---|---|
| Tris [mM] | NaCl [mM] | arginine [wt %] | pH | total HMW [%] | antibody [%] | total HMW [%] | recovery [%] |
| 25 | 100 | 40 | 8.0 | 4.4 | 93.7 | 1.9 | 100 |
| 25 | 250 | 40 | 8.0 | 1.4 | 97.2 | 1.4 | 81 |
| 25 | 175 | 40 | 8.9 | 2.2 | 96.5 | 1.3 | 84 |
| 162.5 | 100 | 40 | 8.9 | 2.8 | 95.4 | 1.9 | 95 |
| 162.5 | 250 | 40 | 7.1 | 1.2 | 96.9 | 2.0 | 57 |
| 162.5 | 175 | 40 | 8.0 | 1.3 | 97.0 | 1.7 | 74 |
| 162.5 | 100 | 40 | 7.1 | 2.8 | 96.1 | 1.0 | 80 |

Example 5

Figure 4:
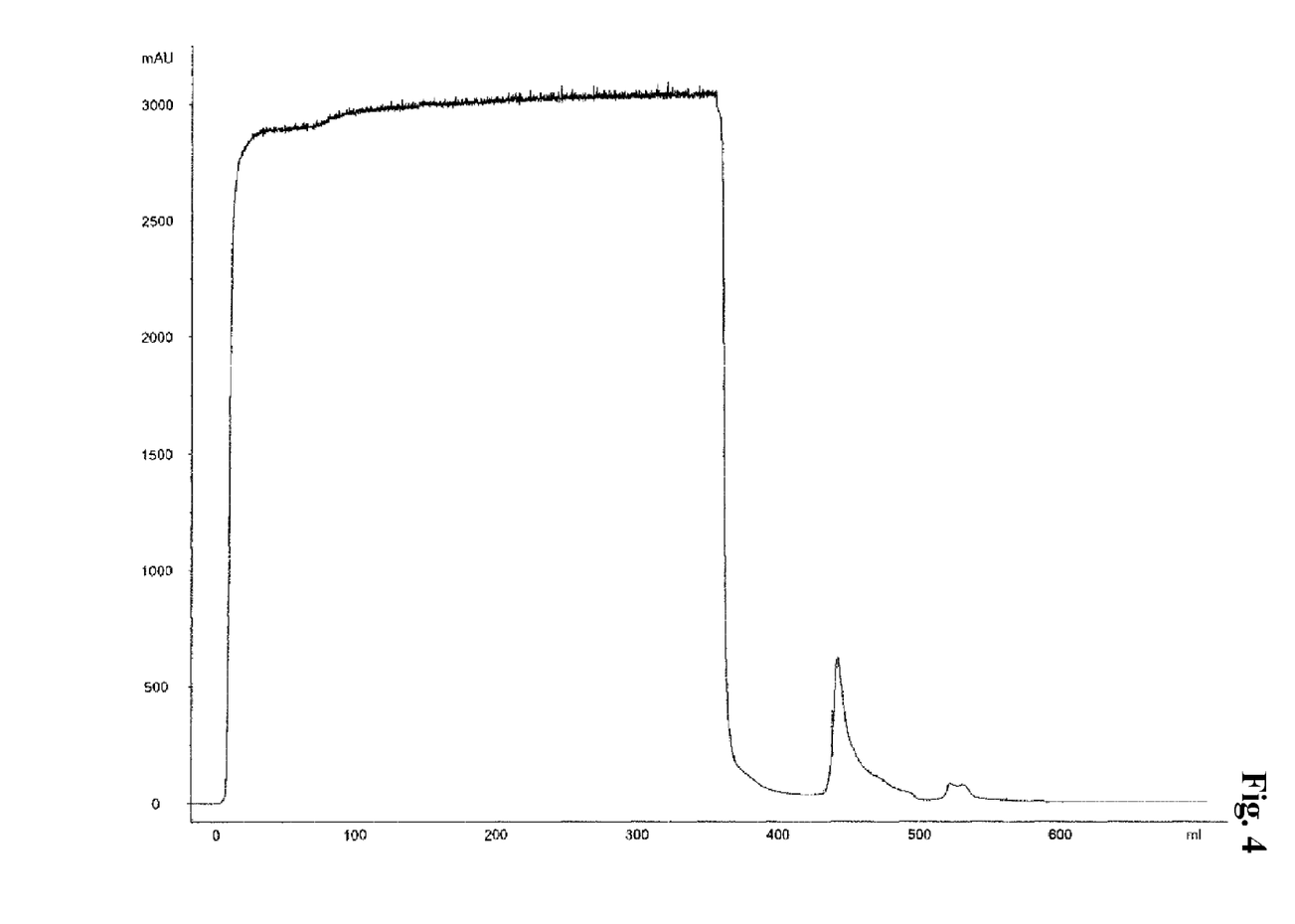
FIG. 4 Elution chromatogram of an application of a crude cultivation supernatant comprising anti-IL 13R antibody.

Comparative Example an Anti-IL13R Antibody with no Pre-Conditioning of the Crude Cultivation Supernatant The chromatography was performed with the following parameters:
resin: Capto™ MMC
column diameter: 1 cm
bed height: 10 cm
applied solution: crude cell cultivation supernatant
load: 21 mg antibody per ml of material
step a-1) 70 mM potassium phosphate, pH 7.3, 10.9 mS/cm
step a-b) 70 mM potassium phosphate, pH 7.3, 10.9 mS/cm
step b) 1M KCl, pH 3.0, 105.6 mS/cm
elution method: step elution
flow rate: 150 cm/h 88% of the applied antibody was not bound to the chromatography material and was found in the flow through (FIG. 4).

Example 6

Figure 5:
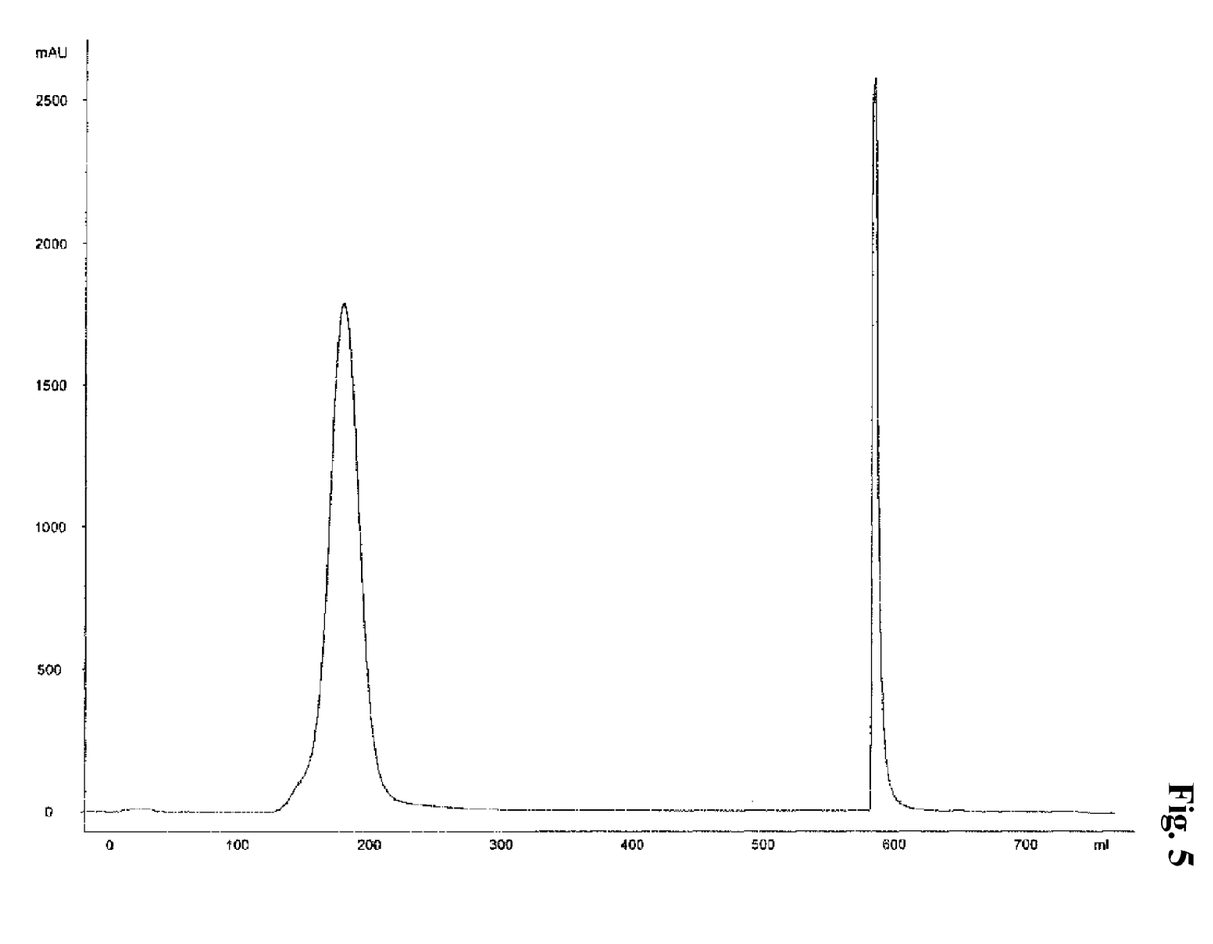
FIG. 5 Elution chromatogram of an application of a pre conditioned cultivation supernatant comprising anti-IL 13R antibody.

Comparative Example an Anti-IL13R Antibody with Pre-Conditioning of the Crude Cultivation Supernatant The chromatography was performed with the following parameters:
resin: Capto™ MMC
column diameter: 1 cm
bed height: 11 cm
applied solution: cell cultivation supernatant adjusted to 1.4 mS/cm
load: 20 mg antibody per ml of material
step a-1) 10 mM potassium phosphate, pH 6.5, 1.4 mS/cm
step a-b) 10 mM potassium phosphate, pH 6.5, 1.4 mS/cm
step b) 100 mM potassium phosphate, pH 7.5, 14.9 mS/cm
elution method: linear gradient
flow rate: 150 cm/h In the chromatogram (FIG. 5) a sharp peak can be seen. The obtained antibody had a purity of 96.6% with a yield of 68%.

The invention claimed is:

1. A method for producing an anti-IGF-1R antibody comprising the following steps:
 a) applying a crude mammalian cell culture cultivation supernatant to a multimodal weak cation exchange chromatography material,
 b) recovering the anti-IGF-1R antibody by applying a buffered solution comprising ethylene glycol and an inorganic salt to the multimodal weak cation exchange chromatography material and thereby producing an anti-IGF-1R antibody.

2. The method according to claim 1, wherein the method comprises the following additional step a-1) prior to step a):
 a-1) applying a buffered solution comprising an inorganic salt to the multimodal weak cation exchange chromatography material.

3. The method according to claim 1 wherein the method comprises the following additional step a-b) after step a) and prior to step b):
 a-b) applying a buffered solution to the multimodal weak cation exchange chromatography material, whereby the anti-IGF-1R antibody is not recovered from the multimodal weak cation exchange chromatography material.

4. The method according to claim 3, wherein the step a-b) comprises two steps a-b1) and a-b2):
 a-b1) applying a buffered solution comprising an inorganic salt to the multimodal weak cation exchange chromatography material, and
 a-b2) applying a buffered solution comprising a denaturant to the multimodal weak cation exchange chromatography material,
 whereby the anti-IGF-1R antibody is not recovered from the multimodal weak cation exchange chromatography material.

5. The method according to claim 4 wherein the denaturant is selected from guanidinium hydrochloride, and urea.

6. The method according to claim 1 wherein the inorganic salt is selected from sodium, chloride, potassium chloride, and ammonium chloride.

7. The method according to claim 1 wherein the buffered solution in step b) comprises 20 mM to 30 mM Tris, 1050 mM to 1350 mM sodium chloride, and about 20% (w/v) ethylene glycol at a pH value of from pH 7.1 to pH 7.3.

8. The method according to claim 2, wherein the buffered solution in step a-1) comprises 20 mM to 30 mM Tris, and 80 mM to 120 mM sodium chloride at a pH value of from pH 7.1 to pH 7.3.

9. The method according to claim 4, wherein the buffered solution in step a-b1) comprises 20 mM to 30 mM Tris, and 80 mM to 120 mM sodium chloride at a pH value of from pH 7.1 to pH 7.3.

10. The method according to claim 4 wherein the buffered solution in step a-b2) comprises 110 mM to 140 mM Tris, 80 mM to 120 mM sodium chloride, and 30 mM to 40 mM arginine at a pH value of from pH 7.1 to pH 7.3.

11. The method according to claim 1 wherein the multimodal weak cation exchange chromatography material comprises cross-linked agarose to which a carboxylic acid, ether, thioether and aromatic functional group containing multimodal weak cation exchange ligand is covalently attached.

* * * * *